(12) United States Patent
Herrmann et al.

(10) Patent No.: US 6,310,234 B1
(45) Date of Patent: Oct. 30, 2001

(54) ESTERS OF AROMATIC POLYCARBOXYLIC ACIDS WITH 2-ALKYLALKAN-1-OLS

(75) Inventors: Albert Thomas Herrmann, Averlak; Jörg Fahl, Hattorf, both of (DE)

(73) Assignee: RWE-DEA Aktiengesellschaft fuer Mineraloel und Chemie (DE)

( * ) Notice: Subject to any disclaimer, the term of this patent is extended or adjusted under 35 U.S.C. 154(b) by 0 days.

(21) Appl. No.: 09/486,526

(22) PCT Filed: Aug. 7, 1998

(86) PCT No.: PCT/DE98/02343

§ 371 Date: Feb. 28, 2000

§ 102(e) Date: Feb. 28, 2000

(87) PCT Pub. No.: WO99/11599

PCT Pub. Date: Mar. 11, 1999

(30) Foreign Application Priority Data

Aug. 29, 1997 (DE) .............................................. 197 37 793

(51) Int. Cl.$^7$ ...................................................... C07C 69/76
(52) U.S. Cl. ...................................................................... 560/76
(58) Field of Search .................................................. 560/76

(56) References Cited

U.S. PATENT DOCUMENTS 4,543,420   9/1985   Godwin et al. .

FOREIGN PATENT DOCUMENTS

| 0157583 A2 | 10/1985 | (EP) . |
| 06136374 | 5/1994 | (JP) . |
| WO 91/07459 | 5/1991 | (WO) . |

*Primary Examiner*—Paul J. Killos
(74) *Attorney, Agent, or Firm*—Browning & Bushman P.C.

(57) ABSTRACT

The invention relates to esters of certain benzene polycarboxylic acids with 2-alkylalcohols, and their use as hydraulic fluid, as or in lubricant formulations or as an additive in cosmetics.

7 Claims, No Drawings

ESTERS OF AROMATIC POLYCARBOXYLIC ACIDS WITH 2-ALKYLALKAN-1-OLS

BACKGROUND OF THE INVENTION

1. Field of the Invention

This invention concerns esters of benzenepolycarboxylic acids with branched aliphatic alcohols and their use as hydraulic fluid, lubricants or cosmetic additives.

2. Description of the Prior Art

Esters have long been known as lubricants. They are used on a large scale as lubricating oils and greases for aircraft engines, for example. Mainly the reaction products of simple monocarboxylic acids with C8 through C10 alcohol mixtures such as those obtained in oxo synthesis, hydrogenation or aldol condensation are used. Complex esters obtained by esterification with dicarboxylic acids and/or glycols are added to the simple ester oils to improve their viscosity, shear stability and lubricant behavior. Ester oils are also used in lubricant greases such as metal soaps or silicones.

The alcohols typically used for esterification are available by oxo synthesis, for example. These alcohols are not chemically uniform and are in the form of isomer mixtures.

Ester oils are characterized by low vapor pressures, a high oxidation stability, good temperature-viscosity characteristics and high aging stability. For certain applications, they must have good miscibility with the desired operating medium. The operating medium may be, for example, pure hydrocarbons, fluorochlorocarbons or fluorocarbons. The ester may also be optimized with regard to low temperature behavior (solubility, pour point) and with regard to heat stability (flash point). Additional requirements are necessitated for compatibility with contact materials such as plastics, metals or paint coatings as required for the application. Ester oils usually have a good high-pressure capacity and load-bearing capacity.

Ester oils of aromatic polycarboxylic acids are known per se. European Patent Application 0 157 583-A2 describes the use of trimellitic acid esters synthesized from linear and/or branched primary alcohols, especially C8 through C10 alcohols. According to European Patent Application 0 157 583-A2 exclusive use of branched alcohols leads to an undesirably high viscosity and a low oxidation stability.

SUMMARY OF THE INVENTION

The object of the present invention is to make available ester oils which meet special requirements with regard to viscosity, the viscosity-temperature characteristics and the high-temperature stability, especially with regard to oxidation stability as well as hydrolysis stability and especially with regard to load tolerance despite the excellent lubricant properties.

DESCRIPTION OF THE PREFERRED EMBODIMENTS

This invention concerns the esters of aromatic polycarboxylic acids with three or four carboxyl groups. The esters according to the present invention and the mixtures thereof can be described by the following structure:

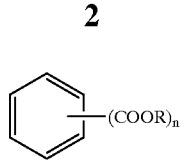

wherein n denotes an integer from 3 to 4 and

R denotes a C12 through C40 hydrocarbon moiety having the following structure:

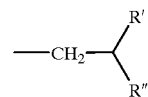

wherein

R' denotes an unbranched C6 through C37 hydrocarbon residue and

R" denotes a C1 through C20 hydrocarbon moiety, where R, R' and R" may be different for each n.

These are preferably the esters of trimellitic acid, trimesic acid and/or pyromellitic acid. Trimellitic acid is also known as 1,2,4-benzenetricarboxylic acid and has the following structure:

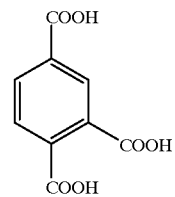

Trimesic acid is likewise an aromatic tricarboxylic acid and is also known as 1,3,5-tricarboxylic acid:

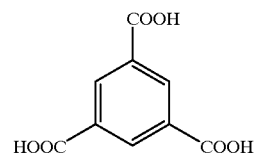

Pyromellitic acid is also known as 1,2,4,5-benzenetetracarboxylic acid and has the following structure:

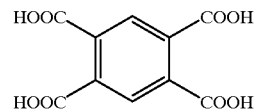

The acids indicated above can be obtained by oxidation from suitably substituted polyalkylbenzenes, optionally in the presence of catalysts such as vanadium pentoxide or manganese catalysts. Trimellitic acid esters and pyromellitic acid esters are especially preferred.

The alcohol group has a 2-alkyl branch. The corresponding alkylalkan-1-ols are accessible by the Guerbet reaction, for example, or oxo synthesis.

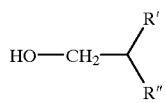

The alkyl group (R) of the alcohol group is preferably a C12 through C36 hydrocarbon residue, especially preferably a C12 through C28 hydrocarbon residue, where R' is a C6 through C26 hydrocarbon residue, especially a C6 through C22 hydrocarbon residue, and R" is a C1 through C18 hydrocarbon residue, especially a C3 through C16 hydrocarbon residue. Both hydrocarbon residues are preferably saturated residues, and R" is preferably an unbranched (linear) hydrocarbon.

These esters should preferably have, independently of one another, a flash point (DIN ISO 2592) of more than 270° C., a solidification point of less than minus 40° C., preferably less than minus 45° C., and a viscosity index (DIN ISO 2909) of more than 100.

The esters according to this invention and compositions containing such esters are used as lubricants or lubricant additives, as cosmetic additives or as hydraulic fluid for transmission of forces. Use as lubricants for industrial gears, for metalworking (e.g., as a rolling oil), as a transmission fluid for processing plastics or textiles and/or as a cooling lubricant (refrigerator oil).

The esters according to this invention are accessible especially easily from the anhydrides or the aromatic polycarboxylic acids, but they can also be synthesized directly from the acids. Esterification is usually performed with the addition of a catalyst, such as an alkyl titanate, with dehydration.

The esters according to this invention can be used as lubricants in combination with other esters, especially neopentyl polyols or silicones for example. Likewise, the ester oils according to this invention can be used as the operating medium themselves or in combination with other operating media, e.g., in the sense of a hydraulic fluid.

Despite the good properties of the ester oils according to this invention, it may be expedient to add additives, such as agents to improve wear, agents to improve the viscosity index, antioxidants, high-pressure additives and corrosion inhibitors, dispersants or metal deactivators.

EXAMPLES

The following 2-alkylalkan-1-ols were used as educts:

TABLE 1

| 2-Alkylalkan-1-ols | | |
|---|---|---|
| Isofol ® 12 | >95 mol% | 2-butyloctanol |
| Isofol ® 14T | 10–20 mol% | 2-butyloctanol |
| | 45–55 mol% | 2-hexyloctanol/2-butyldecanol |
| | 25–35 mol% | 2-hexyldecanol |
| | >95 mol% | (total) |
| Isofol ® 16 | >97 mol% | 2-hexyldecanol |
| Isofol ® 20 | >97 mol% | 2-octyldodecanol |
| Isofol ® 32 | >90 mol% | 2-tetradecyloctadecanol |

Isofol® is a registered trademark of RWE-DEA AG für Mineraloel und Chemie [RWE-DEA Mineral Oil and Chemistry Company]. The alcohols listed above are commercially available as products of Condea Chemie GmbH [Condea Chemical Co.].

2-Alkylalkan-1-ol Trimellitates

Trimellitic anhydride was esterified in high yields with the corresponding alcohols in 10 mol % excess by adding 0.15 wt % isopropyl titanate as the catalyst at a temperature of 170° C. After isolation, colorless, odorless liquids were obtained. The products can be characterized as follows:

TABLE 2

| | | Trimellitic acid esters | | | | |
|---|---|---|---|---|---|---|
| | | T12 | T14 | T16 | T20 | T32 |
| Carbon number | | 45 | 51 | 57 | 69 | 105 |
| Molecular weight | g/mol | 714 | 810 | 882 | 1050 | 1566 |
| Acid value | mg KOH/g | 0.02 | 0.03 | 0.12 | 0.06 | 0.78 |
| Saponification value | mg KOH/g | 236 | 209 | 193 | 150 | 107 |
| Density at 20° C. | g/cm$^3$ | 0.946 | 0.934 | 0.927 | 0.91 | 0.865 |
| Dynamic viscosity at 20° C. | mPas | 443 | 429 | 426 | 453 | 191$^+$ |
| Kinematic viscosity* at 20° C. | mm$^2$/s | 395 | 403 | 403 | 437 | — |
| Kinematic viscosity at 40° C. | mm$^2$/s | 122.6 | 129.6 | 133.3 | 148.3 | 226 |
| Kinematic viscosity* at 100° C. | mm$^2$/s | 13.5 | 14.9 | 16 | 18.4 | 26.1 |
| Viscosity index | — | 106 | 117 | 127 | 139 | 148 |
| Melting range | ° C. | −46 | −45 | −48 | −48 | +19 |
| Solidification range | ° C. | −47 | −46 | −48 | −48 | +16 |
| Flash point | ° C. | 270 | 280 | 275 | 280 | 317 |
| Smoke point | ° C. | 205 | 205 | 200 | 200 | 235 |
| Hydrolysis stability | %hydrolyzed | 21.7 | 20 | 22.7 | 23.8 | 19.6 |
| Acid value after 7 days at 150 ° C. | mg KOH/g | 51.2 | 41.5 | 33.1 | 29 | 16.2 |

The number following the "T" denotes the number of the startinq Isofol ® and indicates the carbon number of the alcohol group. T stands for trimellitate.
*according to Ubbelohde, + at 40° C.

2-Alkylalkan-1-ol Pyromellitates

Pyromellitic anhydride was esterified with the corresponding alcohols in 10 mol % excess with high yields by adding 0.15 wt % isopropyl titanate as the catalyst at a temperature of 170° C.–180° C. The products can be characterized as follows:

TABLE 3

Pyromellitic acid esters

| | | P12 | P14 | P16 | P20 | P32 |
|---|---|---|---|---|---|---|
| Carbon number | | 58 | 66 | 74 | 90 | 138 |
| Molecular weight | g/mol | 926 | 1054 | 1150 | 1374 | 2036 |
| Acid value | mg KOH/g | 0.04 | 0.04 | 0.01 | 0.03 | 0.04 |
| Saponification val | mg KOH/g | 243 | 221 | 197 | 165 | 103 |
| Density at 20° C. | g/cm³ | 0.947 | 0.933 | 0.926 | 0.906 | 0.872 |
| Dynamic Viscosity at 20 ° C. | mPas | 771 | 700 | 657 | 654 | 250⁺ |
| Kinematic viscosity* at 20 ° C. | mm²/s | 709 | 658 | 625 | 650 | — |
| Kinematic viscosity* at 40 ° C. | mm²/s | 210 | 204 | 201 | 211 | 253 |
| Kinematic viscosity* at 100 ° C. | mm²/s | 20.3 | 21.4 | 22.4 | 23.4 | 29.1 |
| Viscosity index | — | 112 | 125 | 135 | 136 | 153 |
| Melting range | ° C. | −43 | −43 | −47 | −44 | 37 |
| Solidification range | ° C. | −43 | −44 | −47 | −44 | 23 |
| Flash point | ° C. | 265 | 275 | 273 | 292 | 315 |
| Smoke point | ° C. | 195 | 235 | 235 | 157 | 170 |
| Hydrolysis stab. | % hydrolyzed | 24.1 | 23.8 | 22.7 | 23.8 | 19.6 |
| Acid value after 7 days at 150 ° C. | mg KOH/g | 43.8 | 38.1 | 33.1 | 29.0 | 16.2 |

The number following the "P" denotes the number of the starting Isofol ® and indicates the carbon number of the alcohol group. P stands for pyromellitate.
*according to Ubbelohde, + at 40 ° C.

What is claimed is:

1. An ester of the formula

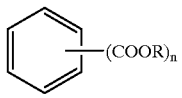

wherein n is 3 or 4 and R is a $C_{12}$ through $C_{40}$ hydrocarbon residue having the following structure:

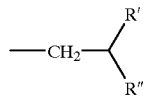

wherein R' is an unbranched $C_6$ through $C_{37}$ hydrocarbon residue and R" is a $C_1$ through $C_{20}$ hydrocarbon moiety, wherein R, R' and R" may be the same or different for each value of n.

2. An ester according to claim 1, wherein the ester is formed from an acid selected from trimellitic acid, trimesic acid pyromellitic acid and mixtures thereof.

3. An ester according to any one of claims 1 or 2, wherein R is a $C_{12}$ through $C_{36}$ hydrocarbon residue, R' is a $C_6$ through $C_{26}$ hydrocarbon residue and R" is a $C_1$ through $C_{18}$ hydrocarbon residue.

4. An ester according to any one of claims 1 or 2, wherein R is a $C_{12}$ through $C_{28}$ hydrocarbon residue, R' is a $C_6$ through $C_{22}$ hydrocarbon residue and R" is a $C_3$ through $C_{16}$ hydrocarbon residue.

5. An ester according to any one of claims 1 or 2, wherein R' and R" are saturated hydrocarbon residues.

6. An ester according to any one of claims 1 or 2, wherein R" is an unbranched hydrocarbon residue.

7. A composition consisting of esters according to claims 1 or 2.

* * * * *